United States Patent [19]

Spaeth

[11] Patent Number: 5,036,198
[45] Date of Patent: Jul. 30, 1991

[54] MULTICOMPONENT PHOTOMETER

[75] Inventor: Tilmann Spaeth, Ernatsreute, Fed. Rep. of Germany

[73] Assignee: Bodenseewerk Perkin-Elmer GmbH (BSW), Fed. Rep. of Germany

[21] Appl. No.: 374,439

[22] Filed: Jun. 30, 1989

[51] Int. Cl.[5] .................. G01N 21/25; G01N 21/03
[52] U.S. Cl. ................................ 250/343; 250/339; 250/351
[58] Field of Search ............... 250/343, 339, 351, 373; 356/418, 51

[56] References Cited

U.S. PATENT DOCUMENTS

| | | | |
|---|---|---|---|
| 2,926,253 | 2/1960 | Munday | 250/343 |
| 3,860,344 | 1/1975 | Garfunkel | 356/51 |
| 3,869,613 | 3/1975 | Link et al. | 250/343 |
| 3,968,367 | 7/1976 | Berg | 250/339 |
| 4,445,359 | 5/1984 | Smith | 250/343 |
| 4,641,973 | 2/1987 | Nestler et al. | 356/418 |
| 4,678,914 | 7/1987 | Melrose et al. | 250/343 |

*Primary Examiner*—Constantine Hannaher
*Assistant Examiner*—Edward J. Glick
*Attorney, Agent, or Firm*—Lee, Mann, Smith, McWilliams & Sweeney

[57] ABSTRACT

A multicomponent photometer comprises a light source (10) emitting a continuum and from which a measuring light beam (12) originates. The measuring light beam (12) passes through a sample vessel (14) in which a sample gas can be introduced. A plurality of first gas vessels (26), which are filled with different gases looked for in the sample gas, and one or several second gas vessels (28), each of which is associated with at least one of the first gas vessels (26) and contains a reference gas, are located in a first filter wheel (22) and are optionally movable into the path of rays of the measuring light beam (12). One or several filters (32), each of which transmits only a limited spectral region about an absorption band of a gas contained in a first gas vessel (26) (blocking filter), are located in a second filter wheel (24) through which one of the filters (32) is optionally movable into the path of rays of the measuring light beam. The measuring light beam (12) is applied to a detector (36). The filter wheels (22,24) are controlled such that one and the same blocking filter (32) is arranged in the path of rays of the measuring light beam (12) in connection with the associated first gas filter (26) and in connection with the second gas filter (28) which is associated with this first gas filter (26).

1 Claim, 6 Drawing Sheets

MULTICOMPONENT PHOTOMETER

BACKGROUND OF THE INVENTION

The invention relates to a multicomponent photometer, comprising (a) a light source emitting a continuum and from which a measuring light beam originates, (b) a sample vessel in which a sample gas can be introduced and through which the measuring light beam passes, (c) a plurality of first gas vessels which are filled with different gases looked for in the sample gas, (d) one or several second gas vessels, each of which is associated with at least one of the first gas vessels and contains a reference gas, (e) one or several filters, each of which transmits only a limited spectral region about an absorption band of a gas contained in a first gas vessel (blocking filter), (f) a detector to which the measuring light beam is applied, and (g) switching means which are arranged to optionally move into the path of rays of the measuring light beam a first gas vessel with an associated blocking filter for providing a measuring path of rays, or a second gas vessel with an associated blocking filter for providing a reference path of rays.

Multicomponent photometers of this type serve to determine the concentration or the partial pressure of a gas looked for in a gas mixture forming the sample gas. The gas looked for in the sample gas absorbs at a certain absorption band. Therefore, after the measuring light beam has passed through the sample vessel, the more the measuring light beam is weakened in the wave range of the absorption band, the higher the partial pressure of the looked-for gas is in the gas mixture of the sample gas. If this weakened measuring light beam then passes through a "gas filter", i.e. one of the first gas vessels which is filled with the gas looked for, the measuring light beam will be further weakened in this wave range. If, however, after switching over, the weakened measuring light beam, instead of passing through the first gas vessel, passes through a second gas vessel which is filled with a reference gas and does not contain the gas looked for, no further weakening will be effected. The smaller the difference between the intensities obtained with the "measuring path of rays" with the first gas vessel and the "reference path of rays" with the second gas vessel, the more the measuring light beam has already been weakened in the sample vessel. If the sample gas does not contain the looked-for gas at all, in the ideal case the measuring light beam is not at all absorbed in the region of said absorption band. The absorption of the concerned wave range in the first gas vessel is very strong in terms of the absolute values of the intensity. Thus, a considerable difference results between the measuring path of rays in which this absorption take place and the reference path of rays in which a second gas vessel is arranged, and the wave lengths of the absorption band of the gas looked for are not absorbed. If, on the other hand, the gas looked for is contained with high partial pressure in the sample gas, the measuring light beam is almost completely absorbed in the wave range of the absorption band. Then it makes no difference in the intensities falling on the detector as to whether the first gas vessel or the second gas vessel is located in the path of rays of the measuring light beam.

It should be noted that the expressions "measuring path of rays" and "reference path of rays" refer herein to one single geometrically unchanged measuring light beam into which only different optical components are inserted.

Because the absorption band of a gas looked for covers only a narrow region of the total spectrum, the absorption in the wave range of this absorption band would make up only a small percentage of the total intensity which falls on the detector. Furthermore, disturbances can be caused in that absorption bands of the gas looked for overlap with absorption bands of other gases in some wave ranges. Therefore, additional filters, "blocking filters", are provided which, in each case, transmit from the continuum only a wave length range about a concerned absorption band of the looked-for gas.

In a multicomponent photometer different "first" gas vessels with different looked-for gases and associated "second" gas vessels with appropriate reference gases can be optionally moved into the path of rays of the measuring light beam. Then, one or another component can be optionally determined in the sample gas.

In such mulitcomponent photometers an associated blocking filter has to be provided for each component to be determined. The wave ranges of the absorption bands of the different gases to be determined are different. Correspondingly, the wave length ranges about the absorption bands which are cut out of the continuum are, in general, also different.

In known multicomponent photometers these blocking filters are mounted on a single filter wheel which also carries the first and the second gas vessels. Then, one blocking filter appropriate for the concerned gas vessel is located in front of each gas vessel. This is mechanically simple but requires one blocking filter each for the first and for the second gas vessels associated with a looked-for gas.

In general, however, the transmittal regions of such blocking filters are wide compared to the width of the absorption bands. Because of this, small variations in the filter characteristics such as those which can be caused by temperature variations, for example, can already lead to disturbing signals which reach the magnitudes of the desired signal. Pairs of filters, with which such variations appear in a corresponding way, can only be obtained, if at all, by expensive selection.

Therefore, it is the object of the invention to provide a multicomponent photometer of the above defined type such that variations of the "blocking filters" do not affect the measurement.

SUMMARY OF THE INVENTION

According to the invention this object is achieved in that (h) the switching means comprise sample changing means for moving the first and the second gas vessels into the path of rays of the measuring light beam, and filter changing means separated therefrom for moving the blocking filters into the path of rays of the measuring light beam, and (i) the vessel changing means and the filter changing means are controlled such that one and the same blocking filter is arranged in the path of rays of the measuring light beam in connection with the associated first gas filter and in connection with the second gas filter which is associated with this first gas filter.

Thus, according to the invention, one and the same blocking filter is used for the measuring path of rays and for the reference path of rays in a multicomponent photometer. Thereby, variations in the characteristic of this blocking filter practically do not effect the measurement. Furthermore, only one single blocking filter is required for each gas to be determined. Because such filters are rather expensive, the entire device is less expensive in spite of the increased mechanical expenditure for additional filter changing means and the associated driving mechanisms and controls.

BRIEF DESCRIPTION OF THE DRAWINGS

An embodiment of the invention will now be described in greater detail with reference to the accompanying drawings, wherein.

DETAILED DESCRIPTION OF THE INVENTION

Figure 1:
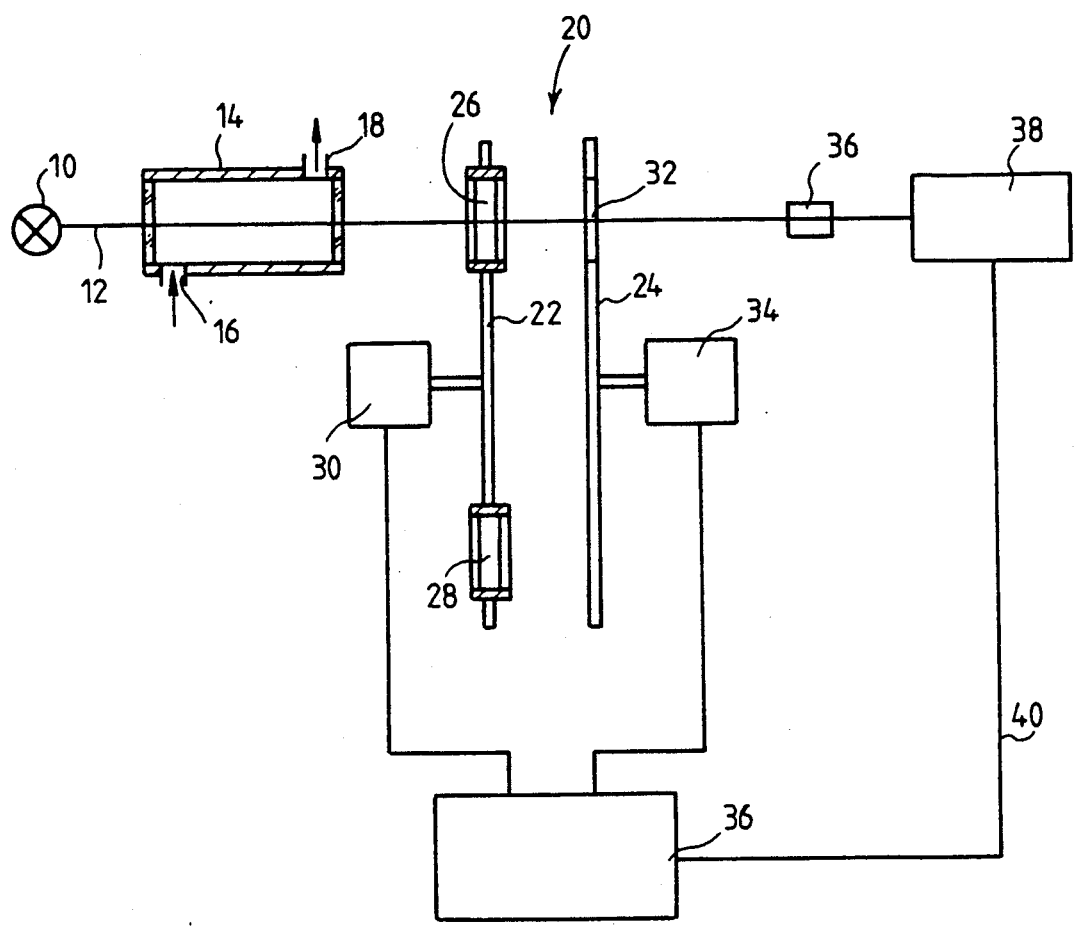
FIG. 1 is a schematic illustration of a mulitcomponent photometer.

In FIG. 1 numeral 10 designates a light source which emits a spectral continuum. A measuring light beam 12 originates from the light source 10. The measuring light beam 12 passes through a sample vessel 14 through which a sample gas in the form of a gas mixture passes. The sample gas enters the sample vessel 14 through an inlet 16 and emerges from the sample vessel 14 through an outlet 18. Switching means 20 are arranged behind the sample vessel 14, through which switching means 20 a measuring path of rays or a reference path of rays can be optionally created. The switching means 20 comprise a first filter wheel 22 and a second filter wheel 24.

A plurality of first gas vessels 26 and one or several second gas vessels 28 are arranged as filters in the first filter wheel 22. Only one first and one second gas vessel threreof can be seen in the schematic illustration of FIG. 1. The filter wheel 22 is arranged to be driven by a servomotor 30.

"Blocking filters" 32 are arranged in the second filter wheel 24. These are filters which transmit only a limited wave length range of a continuum. The filter wheel 24 is arranged to be driven by a servomotor 34.

The two servomotors are connected to a control device 36.

Each of the first gas vessels 26 is filled by a gas looked for and to be determined in the sample gas. A second gas vessel 28 is associated with the first gas vessel 26, which second gas vessel 28 is filled with a reference gas which does not contain the gas looked for and therefore does not absorb in the region of the used absorption band of the gas looked for. A single blocking filter 32 is associated with each pair of first and second gas vessels 26 and 28. The blocking filter 32 can be an interference filter. Of the continuum emitted from the light source 10, the blocking filter transmits only a relatively narrow wave range about the used absorption band of the gas looked for.

Then, the measuring light beam 12 falls on a detector 36 which supplies a signal according to the intensity of the measuring light beam 12. This signal is applied to a signal processing circuit 38. The signal processing circuit 38 receives signals from the control device 36 through the signal path 40, which signals indicate which gas vessel at the moment is located in the path of rays of the measuring light beam. From the measuring values obtained for a certain gas with the measuring path of rays and with the reference path of rays, the signal processing circuit provides a measuring value for the concentration or the partial pressure of the concerned gas in the sample.

The control device 36 controls the filter wheels 22 and 24 through the servomotors 30 and 34 such that one and the same blocking filter 32 is located in the path of rays of the measuring light beam 12 when interposing the first gas vessel 26 of a certain gas and when interposing the associated second gas vessel 28.

The constructive embodiment of the multicomponent photometer is illustrated in FIGS. 2 to 6.

The sample vessel 14 is attached to a partition 46 through bolts 42 and spacers 44. The measuring light beam 12 passes through a window 48. A tube 50 is attached to the sample vessel 14 and extends through an aperture 52 of the partition 46. The measuring light beam 12 extends along the axis of the tube 50.

A second partition 54 is arranged parallel to and spaced from the partition 46. A tube 58 is located in an aperture 56 of the partition 54. The tube 58 is screwed to the partition 54 through bolts 60. The tube 58 is coaxial with the tube 50. A lens 62 is located in the tube 58. Furthermore, the servomotor 30 is attached with an axle 66 to the partition 54.

A filter wheel 22 is located on the axle 66. The filter wheel carries gas vessels of which one gas vessel 26 can be seen in FIG. 2. The gas vessel 26 has a hollow cylindrical mounting 68 in which two parallel windows 70 and 72 are cemented. A filling socket 74 is attached to the mounting 68. After a gas has been filled the filling socket 74 is closed at the tip, e.g. by smelting. A gas is filled in the gas vessel 26, the concentration of which gas in a sample gas shall be determined. A reference gas is filled in a similarly constructed gas vessel 28, which reference gas does not absorb in the region of the absorption band of the gas of the gas vessel 26. The gas vessel 26 is located with its mounting in an aperture 76 of the filter wheel 22 and is attached with screw bolts 78. In the illustrated position of the filter wheel 22 the gas vessel 26 is aligned with the tube 58. The measuring light beam 12 passes through the tube 50, the lens 62 and the tube 58 and through the gas vessel 26.

A light barrier 80 is attached to the partition 54. In a certain position of the filter wheel 22 a flag 82 extends into the light barrier 80, which flag 82 is screwed onto the filter wheel 22. In this way a defined reference position of the filter wheel 22 is obtained, to which position the other positions to be adjusted by the servomotor 30 can be referred.

A further lens 86 is located in a third partition 84 in a mounting 88. The mounting 88 is located in an aperture 90 of the partition 84 and is connected to the partition 84 through screws 92.

A fourth partition 94 carries a housing 96 with the detector 36. The housing 96 is closed by a window 98. The housing 96 is located in an aperture 100 of the partition 94. A cap 101 covers printed cards and electrical components for processing the signal from the detector 36.

Figure 5:
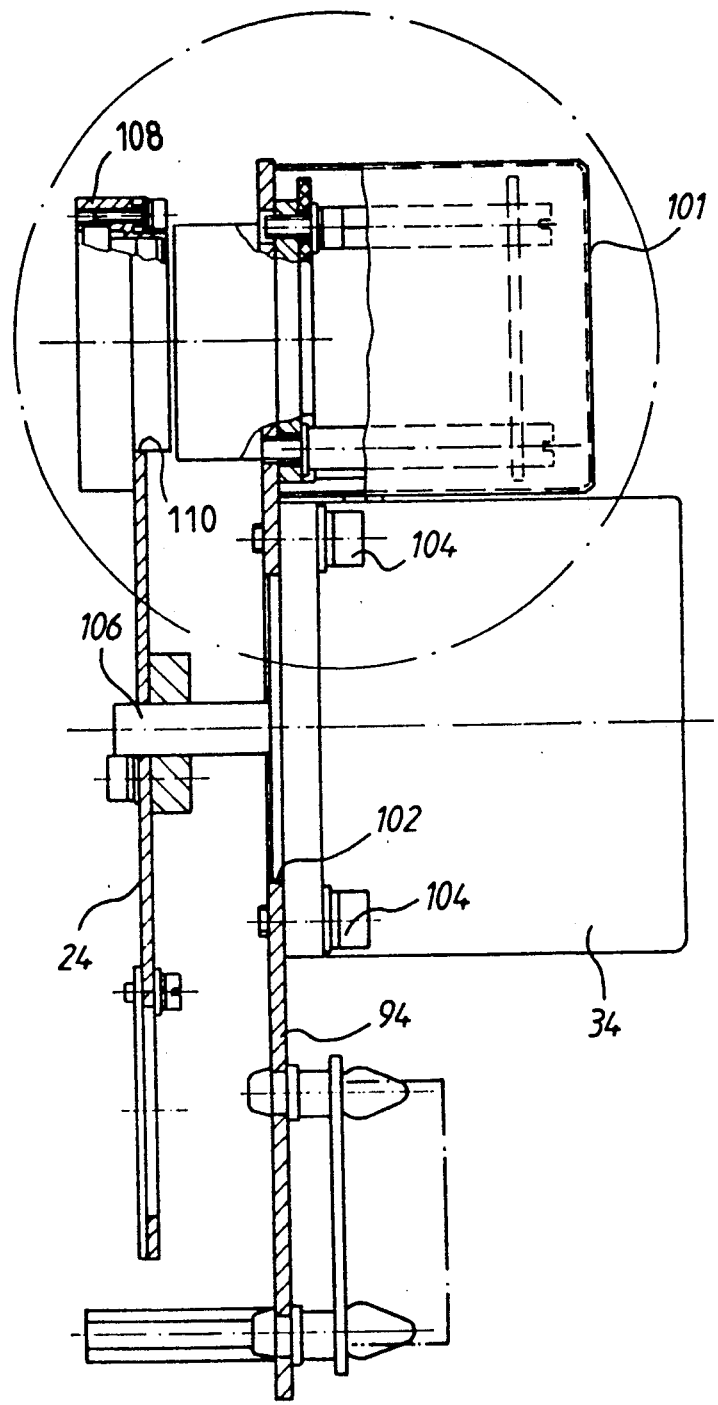
FIG. 5 shows, in detail, a side view of a filter wheel which carries the blocking filters.

As can be best seen in FIG. 5 the servomotor 34 is located on the partition 94 on its side remote from the partition 84. The servomotor 34 is centered in an aperture 102 of the partition 94 and is connected to the partition 94 through screws 104. The filter wheel 24 is located on a shaft 106 of the servomotor 34. The filter wheel 24 carries the blocking filters 32 in the form of interference filters, which are each held in a mounting 108. The mounting 108 of each blocking filter 32 is located in an aperture 110 of the filter wheel 24 and is connected to the filter wheel 24 through screws 112.

Figure 2:
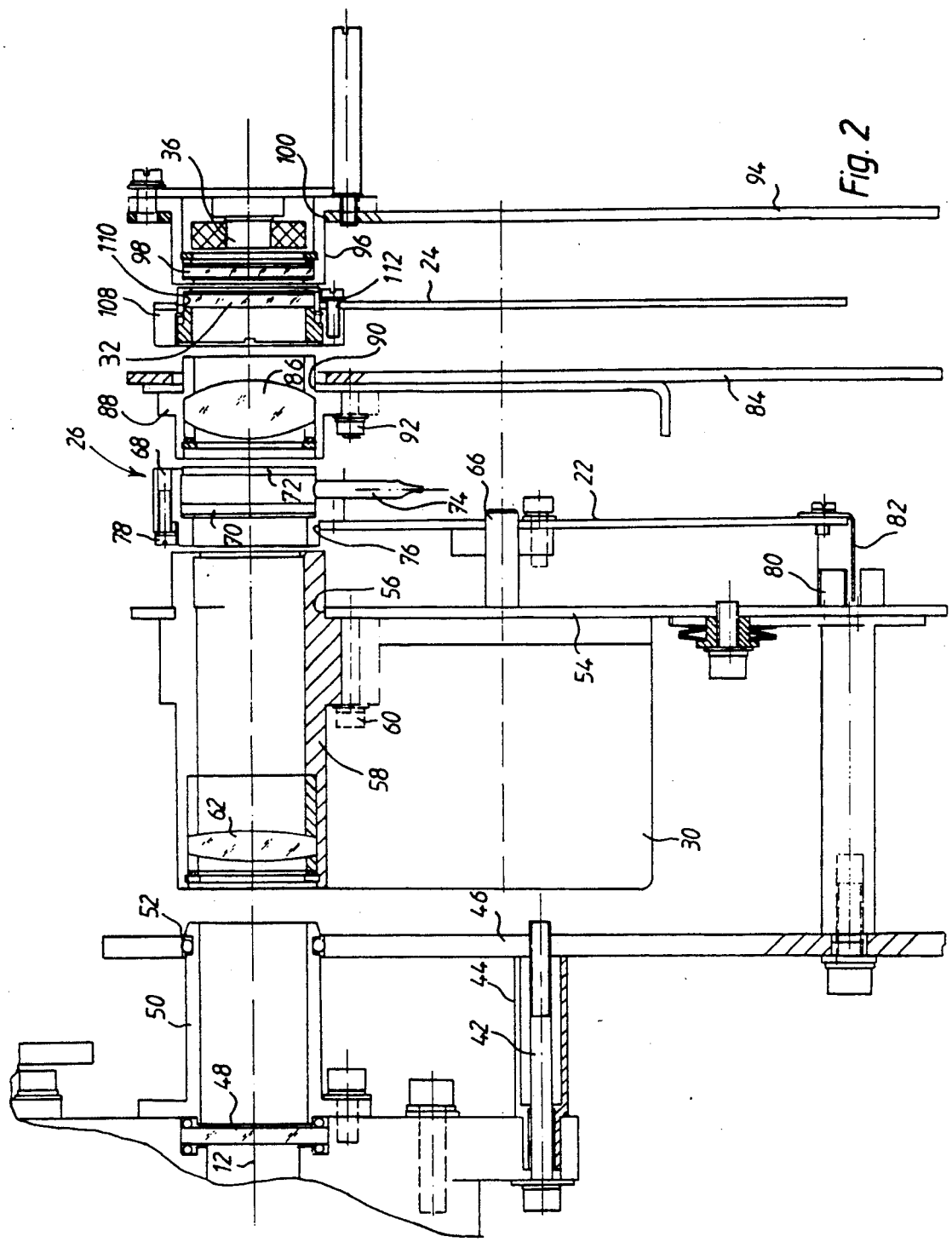
FIG. 2 is a side view of a constructive embodiment of a multicomponent photometer.
Figure 6:
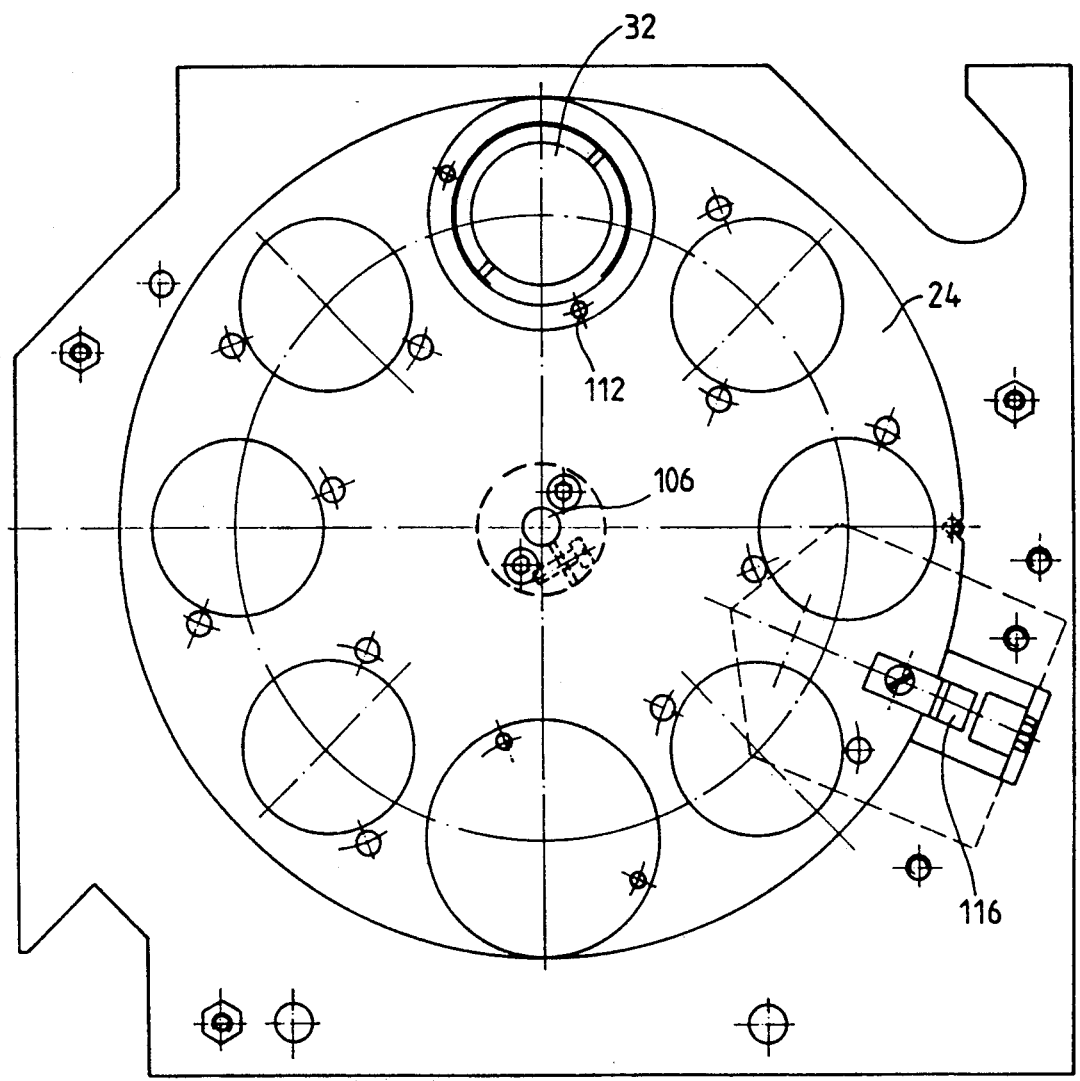
FIG. 6 is a view of the filter wheel of FIG. 5 as seen from the left in FIG. 3.

A light barrier 116 at the partition 94 supplies a reference position for the filter wheel 24 (FIG. 6). The light barrier 116 is constructed in a manner similar to the light barrier 80 (FIG. 2)

Figure 3:
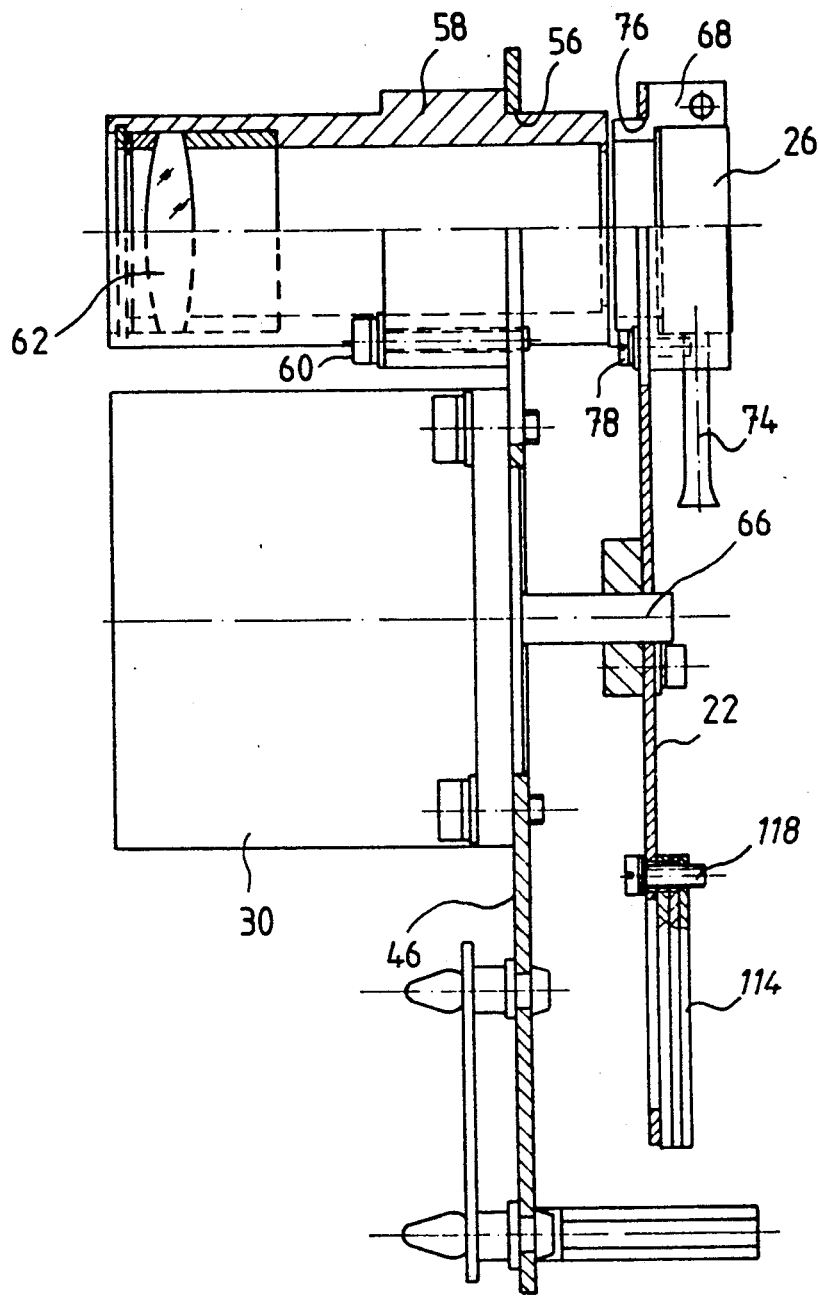
FIG. 3 shows, in detail, a side view of a filter wheel which carries the first and the second gas vessels.
Figure 4:
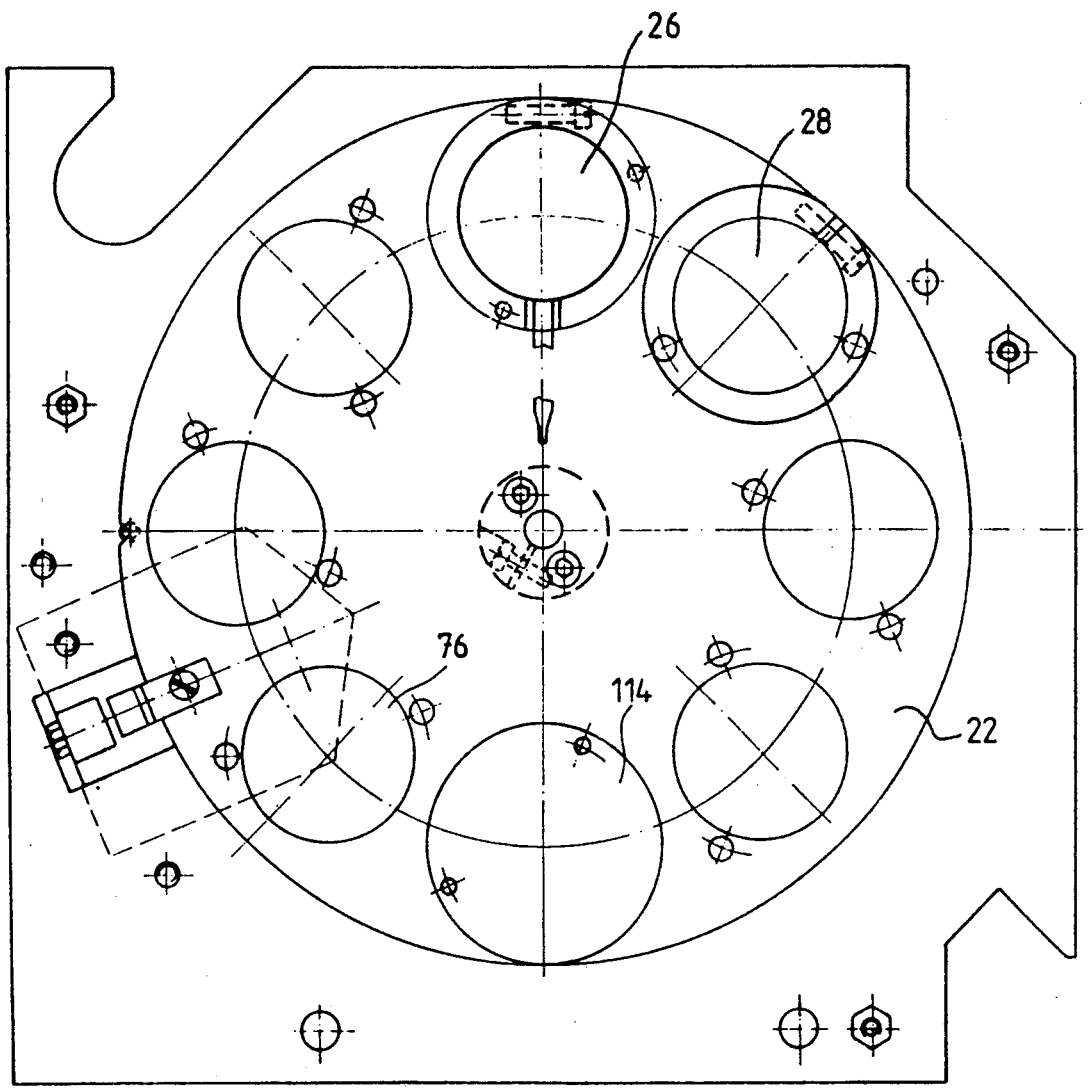
FIG. 4 is a view of the filter wheel as seen from the right in FIG. 3.

As can be seen from FIG. 4 gas vessels 26 and 28 are located beside each other in the filter wheel 22. Only two gas vessels are illustrated in FIG. 4. For static equilibration of the filter wheel 22 balance weights 114 are attached on the opposite sides, of which balance weights only one is drafted. Each balance weight consists of several discs placed upon each other and attached by screws 118 (FIG. 3). However, several gas vessels 26 and 28 can be inserted into the apertures 76 of the filter wheel 22 for determining several components of the sample gas. Moreover, more than one first gas vessel 26 can be associated with a second gas vessel 28.

What is claimed is:
1. Multicomponent photometer, comprising
  (a) a light source (10) emitting a continuum and from which a measuring light beam (12) originates,
  (b) a sample vessel (14) into which a sample gas can be introduced and through which the measuring light beam (12) passes,
  (c) a plurality of first gas vessels (26) which are filled with different gases looked for in the sample gas,
  (d) one or several second gas vessels (28), each of which is associated with at least one of the first gas vessels (26) and contains a reference gas,
  (e) one or several filters (32), each of which transmits only a limited spectral region about an absorption band of a gas contained in a first gas vessel (26) (blocking filter),
  (f) a detector (36) to which the measuring light beam (12) is applied, and
  (g) switching means (20) which are arranged to optionally move into the path of rays of the measuring light beam (12) a first gas vessel (26) with an associated blocking filter (32) for providing a measuring path of rays, or a second gas vessel (28) with an associated blocking filter (32) for providing a reference path of rays,
characterized in that
  (h) the switching means (20) comprise sample changing means formed by a first filter wheel (22), in which the first and the second gas vessels (26,28) are located as filters, for moving the first and the second gas vessels (26,28) into a stationary position in the path of rays of the measuring light beam (12) and filter changing means formed by a second filter wheel (24) separated therefrom for carrying the blocking filters (32) into a stationary position in the path of rays of the measuring light beam (12), and
  (i) the vessel changing means (22) and the filter changing means (24) are controlled such that one and the same blocking filter (32) is arranged in the path of the rays of the measuring light beam (12) in connection with the associated first gas vessel (26) and in connection with the second gas vessel (28) which is associated with this first gas vessel (26).

* * * * *